(12) United States Patent
Sarkar

(10) Patent No.: US 9,901,276 B2
(45) Date of Patent: Feb. 27, 2018

(54) METHOD AND APPARATUS FOR IDENTIFYING SICK SINUS SYNDROME IN AN IMPLANTABLE CARDIAC MONITORING DEVICE

(71) Applicant: Medtronic, Inc., Minneapolis, MN (US)

(72) Inventor: Shantanu Sarkar, Roseville, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 14/926,455

(22) Filed: Oct. 29, 2015

(65) Prior Publication Data

US 2016/0235318 A1    Aug. 18, 2016

Related U.S. Application Data

(60) Provisional application No. 62/117,785, filed on Feb. 18, 2015.

(51) Int. Cl.
*A61B 5/00* (2006.01)
*A61B 5/046* (2006.01)
(Continued)

(52) U.S. Cl.
CPC ............... *A61B 5/046* (2013.01); *A61B 5/04* (2013.01); *A61B 5/04012* (2013.01);
(Continued)

(58) Field of Classification Search
CPC . A61B 5/0452–5/0468; A61N 1/36592; A61N 1/395
See application file for complete search history.

(56) References Cited

U.S. PATENT DOCUMENTS 4,226,245 A    10/1980  Bennett, Jr.
4,374,382 A     2/1983  Markowitz
(Continued)

FOREIGN PATENT DOCUMENTS

EP         2572634        3/2013
WO      2009809241        3/1998
(Continued)

OTHER PUBLICATIONS

Helmet Pürerfellner et al., "P-wave Evidence as a Method for Improving Algorithm to Detect Atrial Fibrillation in Insertable Cardiac Monitors", Heart Rhythm, vol. 11, No. 9, Sep. 2014, pp. 1575-1583.
(Continued)

*Primary Examiner* — Scott Getzow

(57) ABSTRACT

A cardiac monitoring device for determining the occurrence of a sick sinus syndrome condition of a patient that includes a plurality of electrodes to sense a cardiac signal, a sensing module electrically coupled to the plurality of electrodes having circuitry positioned therein to receive the sensed cardiac signal, and a processor coupled to the sensing module and configured to determine an RR interval variability during an RR interval variability session in response to the sensed cardiac signal, determine whether a P-wave occurs during the RR interval variability session, determine whether a sick sinus indicator is satisfied in response to a P-wave occurring, increment a sick sinus count in response to the sick sinus indicator being satisfied, determine whether a sick sinus burden is satisfied in response to the sick sinus count being incremented, and determine the occurrence of sick sinus syndrome in response to the sick sinus burden being satisfied.

20 Claims, 8 Drawing Sheets

(51) Int. Cl.
*A61B 5/04* (2006.01)
*A61B 5/042* (2006.01)
*A61B 5/0452* (2006.01)
*A61B 5/0456* (2006.01)
*A61N 1/362* (2006.01)
*A61N 1/365* (2006.01)
*A61N 1/39* (2006.01)
*A61B 5/0464* (2006.01)

(52) U.S. Cl.
CPC ...... *A61B 5/04014* (2013.01); *A61B 5/04017* (2013.01); *A61B 5/0422* (2013.01); *A61B 5/0452* (2013.01); *A61B 5/0456* (2013.01); *A61B 5/686* (2013.01); *A61N 1/3624* (2013.01); *A61N 1/36507* (2013.01); *A61N 1/36592* (2013.01); *A61N 1/395* (2013.01); *A61N 1/3987* (2013.01); *A61B 5/0464* (2013.01)

(56) References Cited

U.S. PATENT DOCUMENTS

| | | | |
|---|---|---|---|
| 4,721,114 A | 1/1988 | DuFault et al. | |
| 5,117,824 A | 6/1992 | Keimel et al. | |
| 5,193,535 A | 3/1993 | Bardy et al. | |
| 5,292,338 A | 3/1994 | Bardy | |
| 5,312,445 A | 5/1994 | Nappholz et al. | |
| 5,334,221 A | 8/1994 | Bardy | |
| 5,458,623 A | 10/1995 | Lu et al. | |
| 5,466,245 A | 11/1995 | Spinelli et al. | |
| 5,545,186 A | 8/1996 | Olson et al. | |
| 5,609,157 A | 3/1997 | Panescu | |
| 5,609,158 A | 3/1997 | Chan | |
| 5,755,739 A | 5/1998 | Sun et al. | |
| 5,782,888 A | 7/1998 | Sun | |
| 5,817,134 A | 10/1998 | Greenhut et al. | |
| 6,067,473 A | 5/2000 | Greeninger et al. | |
| 6,393,316 B1 | 5/2002 | Gillberg et al. | |
| 6,470,210 B1 | 10/2002 | Chen et al. | |
| 6,516,225 B1 | 2/2003 | Florio | |
| 6,745,068 B2 | 6/2004 | Koyrakh et al. | |
| 6,865,414 B1 | 3/2005 | Levine | |
| 6,895,272 B2 | 5/2005 | Seim et al. | |
| 6,904,315 B2 | 6/2005 | Panken et al. | |
| 6,904,319 B2 | 6/2005 | Seim et al. | |
| 6,912,418 B1 | 6/2005 | Florio | |
| 6,922,584 B2 | 7/2005 | Wang et al. | |
| 6,931,273 B2 | 8/2005 | Groenewegen et al. | |
| 7,031,765 B2 | 4/2006 | Ritscher et al. | |
| 7,062,315 B2 | 6/2006 | Koyrakh et al. | |
| 7,139,604 B1 | 11/2006 | Mouchawar | |
| 7,184,815 B2 | 2/2007 | Kim et al. | |
| 7,187,965 B2 | 3/2007 | Bischoff et al. | |
| 7,242,978 B2 | 7/2007 | Cao et al. | |
| 7,245,965 B1 | 7/2007 | Pei et al. | |
| 7,308,308 B1 | 12/2007 | Xi et al. | |
| 7,412,282 B2 | 8/2008 | Houben | |
| 7,509,160 B2 | 3/2009 | Bischoff et al. | |
| 7,515,956 B2 | 4/2009 | Thompson | |
| 7,532,928 B2 | 5/2009 | Lang | |
| 7,537,569 B2 | 5/2009 | Sarkar et al. | |
| 7,561,911 B2 | 7/2009 | Cao et al. | |
| 7,570,990 B2 | 8/2009 | Faber | |
| 7,580,748 B2 | 8/2009 | Garner | |
| 7,593,766 B2 | 9/2009 | Faber | |
| 7,596,405 B2 | 9/2009 | Kurzweil et al. | |
| 7,623,911 B2 | 11/2009 | Sarkar et al. | |
| 7,627,368 B2 | 12/2009 | Houben et al. | |
| 7,640,054 B2 | 12/2009 | Koyrakh et al. | |
| 7,657,305 B2 | 2/2010 | Nigam | |
| 7,657,307 B2 | 2/2010 | Van Dam et al. | |
| 7,706,869 B2 | 4/2010 | Cao et al. | |
| 7,729,754 B2 | 6/2010 | Cao et al. | |
| 7,826,893 B2 | 11/2010 | Cao et al. | |
| 7,983,742 B2 | 7/2011 | Starc | |
| 7,996,070 B2 | 8/2011 | van Dam et al. | |
| 8,000,778 B2 | 8/2011 | Seim et al. | |
| 8,064,998 B2 | 11/2011 | Good | |
| 8,195,280 B2 | 6/2012 | Van Dam et al. | |
| 8,233,980 B2 | 7/2012 | Pei | |
| 8,265,753 B2 | 9/2012 | Higham | |
| 8,280,510 B2 | 10/2012 | Dyjach | |
| 8,285,377 B2 | 10/2012 | Rosenberg | |
| 8,412,316 B2 | 4/2013 | Seim et al. | |
| 8,428,697 B2 | 4/2013 | Zhang et al. | |
| 8,428,705 B2 | 4/2013 | Kurzweil et al. | |
| 8,521,268 B2 | 8/2013 | Zhang et al. | |
| 8,548,573 B2 | 10/2013 | Keefe | |
| 8,560,058 B2 | 10/2013 | Babaeizadeh et al. | |
| 8,588,895 B2 | 11/2013 | Sanghera et al. | |
| 8,639,316 B2 | 1/2014 | Sarkar | |
| 8,688,469 B2 | 4/2014 | Ziegler et al. | |
| 8,718,750 B2 | 5/2014 | Lian | |
| 8,923,963 B2 | 12/2014 | Bonner et al. | |
| 8,977,350 B2 | 3/2015 | Sarkar et al. | |
| 2003/0023178 A1 | 1/2003 | Bischoff et al. | |
| 2005/0065564 A1 | 3/2005 | Seim et al. | |
| 2005/0080347 A1 | 4/2005 | Sheth et al. | |
| 2006/0074332 A1 | 4/2006 | Bischoff et al. | |
| 2006/0079797 A1 | 4/2006 | Bischoff et al. | |
| 2006/0079798 A1 | 4/2006 | Bischoff et al. | |
| 2006/0106323 A1 | 5/2006 | Bischoff et al. | |
| 2007/0142866 A1 | 6/2007 | Li et al. | |
| 2007/0232944 A1 | 10/2007 | Ghanem et al. | |
| 2008/0147133 A1 | 6/2008 | Garner | |
| 2008/0154318 A1 | 6/2008 | Albus | |
| 2008/0161703 A1 | 7/2008 | Houben et al. | |
| 2009/0216144 A1 | 8/2009 | Hopenfeld | |
| 2009/0270747 A1 | 10/2009 | van Dam et al. | |
| 2010/0030293 A1 | 2/2010 | Sarkar et al. | |
| 2010/0114195 A1 | 5/2010 | Burnes et al. | |
| 2011/0125206 A1 | 5/2011 | Bornzin et al. | |
| 2011/0301661 A1 | 12/2011 | Seim et al. | |
| 2011/0319949 A1 | 12/2011 | Bardy | |
| 2012/0123232 A1 | 5/2012 | Najarian et al. | |
| 2012/0226179 A1 | 9/2012 | Stadler et al. | |
| 2012/0238891 A1 | 9/2012 | Sarkar et al. | |
| 2012/0238892 A1 | 9/2012 | Sarkar | |
| 2012/0290030 A1 | 11/2012 | Warman et al. | |
| 2013/0172765 A1 | 7/2013 | Stewart | |
| 2014/0128758 A1 | 5/2014 | Galloway et al. | |
| 2014/0155722 A1 | 6/2014 | Greenspan et al. | |
| 2014/0276154 A1 | 9/2014 | Katra et al. | |
| 2014/0350422 A1 | 11/2014 | Stewart | |
| 2014/0378851 A1 | 12/2014 | Frei et al. | |
| 2015/0073295 A1 | 3/2015 | Gordon et al. | |
| 2015/0080752 A1 | 3/2015 | Lian et al. | |
| 2015/0105681 A1 | 4/2015 | Bonan et al. | |
| 2015/0230722 A1 | 8/2015 | Sarkar et al. | |
| 2015/0305642 A1 | 10/2015 | Reinke et al. | |
| 2015/0306375 A1 | 10/2015 | Marshall et al. | |
| 2015/0306410 A1 | 10/2015 | Marshall et al. | |

FOREIGN PATENT DOCUMENTS

| | | |
|---|---|---|
| WO | 0180042 A1 | 10/2001 |
| WO | 2004043538 | 5/2004 |
| WO | 2004108212 | 12/2004 |
| WO | 2012058398 | 5/2012 |

OTHER PUBLICATIONS (PCT/US2016/017686) PCT Notification of Transmittal of the International Search Report and the Written Opinion of the International Searching Authority, mailed May 11, 2016, 12 pages.
(PCT/US2016/017683) PCT Notification of Transmittal of the International Search Report and the Written Opinion of the International Searching Authority, mailed Jun. 8, 2016, 6 pages.
Pürerfellner et al., "P-Wave Evidence as a Method for Improving Algorithm to Detect Atrial Fibrillation in insertable Cardiac Monitors", Heart Rhythm, vol. 11, No. 9, Sep. 2014, 9 pages.

(56) References Cited

OTHER PUBLICATIONS

Sarkar et al, "Method and Apparatus for Atrial Arrhythmia Episode Detection", U.S. Appl. No. 14/695,135, filed Apr. 24, 2015, 30 pages.

Sarkar et al, "Method and Apparatus for Atrial Arrhythmia Episode Detection", U.S. Appl. No. 14/695,156, filed Apr. 24, 2015, 42 pages.

Sarkar et al, "Method and Apparatus for Atrial Arrhythmia Episode Detection", U.S. Appl. No. 14/695,171, filed Apr. 24, 2015, 38 pages.

Sarkar et al, "Method and Apparatus for Atrial Arrhythmia Episode Detection", U.S. Appl. No. 14/695,111, filed Apr. 24, 2015, 51 pages.

Cao et al, "Atrial Arrhythmia Episode Detection in a Cardiac Medical Device", U.S. Appl. No. 14/604,363, filed Jan. 23, 2015, 46 pages.

Cao et al, "Atrial Arrhythmia Episode Detection in a Cardiac Medical Device", U.S. Appl. No. 14/604,411, filed Jan. 23, 2015, 48 pages.

Cao et al, "Atrial Arrhythmia Episode Detection in a Cardiac Medical Device", U.S. Appl. No. 14/604,468, filed Jan. 23, 2015, 46 pages.

Zhang et al, "Method and Apparatus for Beat Acquisition During Template Generation in a Medical Device Having Dual Sensing Vectors", U.S. Appl. No. 14/604,111, filed Jan. 23, 2015, 77 pages.

Zhang et al, "Method and Apparatus for Beat Acquisition During Template Generation in a Medical Device Having Dual Sensing Vectors", U.S. Appl. No. 14/604,260, filed Jan. 23, 2015, 75 pages.

Zhang et al, "Method and Apparatus for Beat Acquisition During Template Generation in a Medical Device Having Dual Sensing Vectors", U.S. Appl. No. 15/002,521, filed Jan. 21, 2016, 80 pages.

Sarkar et al, "Method and Apparatus for Adjusting a Threshold During Atrial Arrhythmia Episode Detection in an Implantable Medical Device", U.S. Appl. No. 14/926,419, filed Oct. 29, 2015, 51 pages.

Sarkar et al, "Method and Apparatus for Identifying Sick Sinus Syndrome", U.S. Appl. No. 14/926,455, filed Oct. 29, 2015, 39 pages.

Cao et al, "Atrial Arrhythmia Detection During Intermittent Instances of Ventricular Pacing in a Cardiac Medical Device", U.S. Appl. No. 14/520,798, filed Oct. 22, 2014, 35 pages.

Cao et al, "Atrial Arrhythmia Detection During Ventricular Pacing in a Cardiac Medical Device", U.S. Appl. No. 14/520,847, filed Oct. 22, 2014, 49 pages.

Cao et al, "Atrial Arrhythmia Episode Detection in a Cardiac Medical Device", U.S. Appl. No. 14/520,938, filed Oct. 22, 2014, 47 pages.

Couceiro et al., "Detection of Atrial Fibrillation Using Model-Based ECG Analysis", 19th International Conference on Pattern Recognition, Dec. 2008, 5 pages.

Cao et al., Atrial Arrhythmia Episode Detection in a Cardiac Medical Device, U.S. Appl. No. 15/004,202, filed Jan. 22, 2016, 74 pages.

(PCT/US2016/018389) PCT Notification of Transmittal of the International Search Report and the Written Opinion of the International Searching Authority, dated Jun. 13, 2016, 12 pages.

(PCT/US2016/018496) PCT Notification of Transmittal of the International Search Report and the Written Opinion of the International Searching Authority, dated Jun. 13, 2016, 11 pages.

(PCT/US2016/018383) PCT Notification of Transmittal of the International Search Report and the Written Opinion of the International Searching Authority, dated May 23, 2016, 12 pages.

(PCT/US2016/018408) PCT Notification of Transmittal of the International Search Report and the Written Opinion of the International Searching Authority, dated May 24, 2016, 13 pages.

(PCT/US2016/014493) PCT Notification of Transmittal of the International Search Report and the Written Opinion of the International Searching Authority, dated Apr. 15, 2016, 14 pages.

METHOD AND APPARATUS FOR IDENTIFYING SICK SINUS SYNDROME IN AN IMPLANTABLE CARDIAC MONITORING DEVICE

CROSS-REFERENCE TO RELATED APPLICATIONS

This application claims priority and other benefits of U.S. Provisional Application No. 62/117,785, filed on Feb. 18, 2015, entitled "Method and Apparatus for Atrial Arrhythmia Detection", incorporated herein by reference in its entirety.

TECHNICAL FIELD

The disclosure relates generally to implantable medical devices and, in particular, to a method for and apparatus for identifying sick sinus syndrome in an implantable cardiac monitoring device.

BACKGROUND

During normal sinus rhythm (NSR), the heart beat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (A-V) node. The A-V node responds by propagating a ventricular depolarization signal through the bundle of His of the ventricular septum and thereafter to the bundle branches and the Purkinje muscle fibers of the right and left ventricles.

Atrial tachyarrhythmia includes the disorganized form of atrial fibrillation and varying degrees of organized atrial tachycardia, including atrial flutter. Atrial fibrillation (AF) occurs because of multiple focal triggers in the atrium or because of changes in the substrate of the atrium causing heterogeneities in conduction through different regions of the atria. The ectopic triggers can originate anywhere in the left or right atrium or pulmonary veins. The AV node will be bombarded by frequent and irregular atrial activations but will only conduct a depolarization signal when the AV node is not refractory. The ventricular cycle lengths will be irregular and will depend on the different states of refractoriness of the AV-node.

Sick sinus syndrome, also known as sinus node disease or sinus node dysfunction, is the name for a group of heart rhythm arrhythmias in which the sinus node doesn't work properly. Normally, the sinus node produces a steady pace of regular electrical impulses. In sick sinus syndrome, these signals are abnormally paced and therefore a person with sick sinus syndrome may have heart rhythms that are too fast, too slow, punctuated by long pauses—or an alternating combination of all of these rhythm problems. Many people with sick sinus syndrome eventually need a pacemaker to keep the heart in a regular rhythm. Therefore, what is needed is a method and apparatus for determining the occurrence of sick sinus syndrome of a patient in a cardiac monitoring device.

DETAILED DESCRIPTION

In the following description, references are made to illustrative embodiments for carrying out the methods described herein. It is understood that other embodiments may be utilized without departing from the scope of the disclosure.

The methods presented herein may be embodied in software, hardware or firmware in implantable or external medical devices. Such devices include implantable monitoring devices having cardiac EGM/ECG monitoring capabilities and associated EGM/ECG sense electrodes, which may be intracardiac, epicardial, or subcutaneous electrodes.

The methods described herein can also be incorporated in implantable medical devices having therapy delivery capabilities, such as single chamber or bi-ventricular pacing systems or ICDs that sense the R-waves in the ventricles and deliver an electrical stimulation therapy to the ventricles. The atrial arrhythmia detection methods presently disclosed may also be incorporated in external monitors having ECG electrodes coupled to the patient's skin to detect R-waves, e.g. Holter monitors, or within computerized systems that analyze pre-recorded ECG or EGM data. Embodiments may further be implemented in a patient monitoring system, such as a centralized computer system which processes data sent to it by implantable or wearable monitoring devices, including subcutaneous devices having loop recorders.

Figure 1:
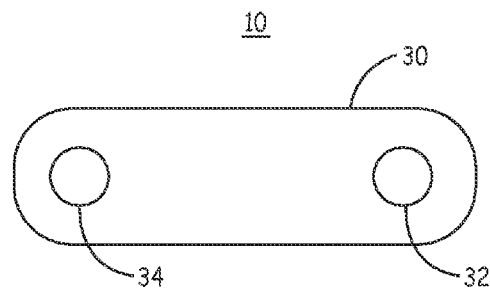
FIG. 1 is a conceptual diagram of an exemplary implantable medical device for determining a sick sinus burden of a patient, according to an embodiment of the present disclosure.

FIG. 1 is a conceptual diagram of an exemplary implantable medical device for determining a sick sinus burden of a patient, according to an embodiment of the present disclosure. As illustrated in FIG. 1, according to an embodiment of the present disclosure, an implantable medical device for determining a sick sinus burden may be embodied as a monitoring device 10 having a proximal electrode 32 and a distal electrode 34 located along a housing 30 of the monitoring device 10, as described for example, in U.S. Patent Publication No. 2015/0073295, incorporated herein by reference in it's entirety. The housing 30 encloses electronic circuitry inside the implantable monitoring device 10 and protects the implantable medical device circuitry contained therein (shown in FIG. 2) from body fluids. Electrical feedthroughs provide electrical connection of electrodes 32 and 34 across the housing 30 to internal circuitry when electrodes 32 and 34 are positioned along the exterior surface of housing 30.

The electrodes 32 and 34 are used to sense cardiac signals for determining an atrial arrhythmia event and a sick sinus burden, described in detail below, e.g. ECG signals, intra-thoracically or extra-thoracically, which may be sub-muscularly or subcutaneously. ECG signals may be stored in a memory 42 (shown in FIG. 2) of the monitoring device 10, and ECG data may be transmitted by the monitoring device 10 via a communication module 46 (shown in FIG. 2) to another medical device, which may be another implantable device or an external device, such as a programmer, for example. In alternative applications, electrodes 32 and 34 may be used for sensing any biopotential signal of interest, which may be, for example, an EGM, EEG, EMG, or a nerve signal, from any implanted location.

Electrodes 32 and 34 may be formed of a biocompatible conductive material, e.g. titanium, platinum, iridium, or alloys thereof. The configuration illustrated in FIG. 1 is just one example electrode configuration. In other instances, sensing electrodes 32 and 34 may be located at other positions along the housing 30 than the positions shown in FIG. 1. For example, the electrodes 32 and 34 are shown both positioned along a top side of the monitoring device 10, but in other examples electrodes 32 and 34 may be located on the bottom side or lateral side of the implantable medical device 10, on opposing sides of the monitoring device 10, or on one or both ends of the monitoring device 10.

Additionally, all or a portion of the housing 30 may function as one of the electrodes and be insulated from any other electrodes positioned along the housing 30. An exemplary description of such a configuration is disclosed in commonly assigned and co-pending U.S. patent application Ser. No. 14/060,649, titled "Supply Noise Rejection In Implantable Medical Devices" (Reinke et al.), incorporated herein by reference in its entirety.

In still other embodiments, an implantable medical device may include one or more electrodes carried by an electrical lead or tether extending away from the implantable medical device and coupled to the implantable medical device internal circuitry via electrical feedthroughs and conductors. In further instances, monitoring device 10 may include more than two electrodes for various monitoring or therapy delivery purposes.

Although illustrated and described throughout this disclosure as being a cardiac monitor, Ithe implantable medical device 10 may be any of number of other implantable devices, including implantable hemodynamic monitors, blood chemistry monitors, pressure monitors, nerve monitors, muscle monitors, brain monitors, or the like. In any of these cases, the implantable medical device 10 may include additional sensors besides electrodes 32 and 34 to monitor desired physiological signals.

Figure 2:
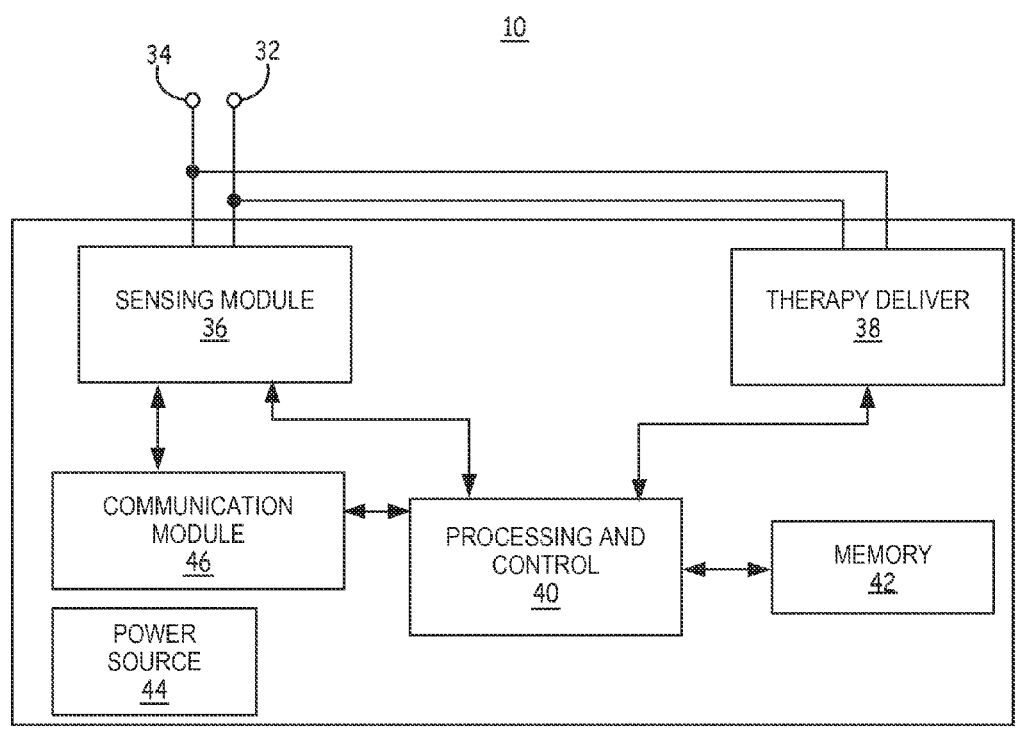
FIG. 2 is a functional schematic diagram of the medical device of FIG. 1, according to an embodiment of the present disclosure.

FIG. 2 is a functional block diagram of the implantable medical device shown in FIG. 1. As illustrated in FIG. 2, the monitoring device 10 includes a cardiac signal sensing module 36 coupled to electrodes 32 and 34 for sensing cardiac signals and monitoring atrial arrhythmia events, such as atrial fibrillation or atrial tachycardia within a patient, as described below.

The monitoring device 10 may be embodied as a monitoring-only device without therapy delivery capabilities. In other examples, the monitoring device 10 may include a therapy delivery module 38, which may be configured to generate electrical pulses for delivering therapeutic electrical stimulation, such as cardiac pacing, nerve stimulation, deep brain stimulation, or other neurostimulation. In such examples, therapy delivery module 38 is coupled to electrodes 32 and 34 for delivering electrical pulses to achieve a therapeutic benefit to the patient in addition to monitoring biopotential and bioimpedance signals of the patient. Sensing cardiac signals during therapeutic stimulation pulse delivery may be temporarily blanked or interrupted to prevent saturation of sensing amplifiers during stimulation pulse delivery. Other examples of therapy delivery capabilities that may be included in therapy delivery module 38 include fluid delivery pumps for delivering a pharmacological agent, biological fluid or other therapeutic fluid.

The sensing module 30 may include an analog amplifier and/or filter for receiving an analog voltage signal from electrodes 32 and 34. The analog voltage signals received from electrodes 32 and 34 are passed to analog-to-digital (ND) converters included in the sensing module 30 or in processing and control module 40. The ND converters provide a sampled, digital signal of the cardiac signal received by the sensing module 30 to processing and control module 40 for further analysis according to a particular clinical application and/or storage in memory 42.

Processing and control module 40 and associated memory 42 control implantable medical device functions and process signals received from electrodes 32 and 34 according to programmed signal analysis routines or algorithms. The monitoring device 10 may include other optional sensors (not shown) for monitoring physiological signals, such as an activity sensor, pressure sensor, oxygen sensor, accelerometer, or other sensor used to monitor a patient.

Processing and control module 40 may control monitoring time intervals and sampling rates according to a particular clinical application. Processing and control module 40 may include state machines or other sequential logic circuitry to control device functions and need not be implemented exclusively as a microprocessor. Processor and control module 40 and sensing module 20 may operate to acquire signal data and store processed or raw signal data in memory 42.

Communication module 46 includes an antenna and wireless transmitter to transmit electrical signal data, e.g. ECG signal data, stored in memory 42 or received from processing and control module 40 in real time. Communication module 46 may be configured to transmit and receive communication signals via inductive coupling, electromagnetic coupling, tissue conductance, Near Field Communication (NFC), Radio Frequency Identification (RFID), BLUETOOTH®, WiFi, or other proprietary or non-proprietary wireless telemetry communication schemes. Communication module enables the monitoring device 10 to communicate with a programmer (not shown) located external to the monitoring device 10 and includes a user interface that presents information to and receives input from a user. It should be noted that the user may also interact with programmer remotely via a networked computing device.

A user, such as a physician, technician, surgeon, electrophysiologist, other clinician, or patient, interacts with programmer to communicate with monitoring device 10. For example, the user may interact with programmer to retrieve physiological or diagnostic information from monitoring device 10. A user may also interact with programmer to program monitoring device 10, e.g., select values for operational parameters of the monitoring device 10. For example, the user may use programmer to retrieve information from monitoring device 10 regarding the rhythm of a patient heart, trends therein over time, or arrhythmic episodes.

Monitoring device 10 and the programmer may communicate via wireless communication using any techniques known in the art.

A power source 44 provides power to each of the modules 36, 38, 40, 46, and memory 42 as needed. Power source 44 may include one or more energy storage devices, such as one or more rechargeable or non-rechargeable batteries.

Modules 36, 38, 40, 46, and memory 42 represent functionality included in the monitoring device 10. Modules of the present disclosure may include any discrete and/or integrated electronic circuit components that implement analog and/or digital circuits capable of producing the functions attributed to the modules herein. For example, the modules may include analog circuits, e.g., pre-amplification circuits, filtering circuits, and/or other analog signal conditioning circuits. The modules may also include digital circuits, e.g., digital filters, combinational or sequential logic circuits, state machines, integrated circuits, a processor (shared, dedicated, or group) that executes one or more software or firmware programs, memory devices, or any other suitable components or combination thereof that provide the described functionality.

Memory 42 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), Flash memory, or any other memory device. Memory 42 may include non-transitory computer readable storage media storing instructions that, when executed by one or more processing circuits, cause the modules to perform various functions attributed to the implantable medical device 10. The storage media may include any computer-readable storage media with the sole exception being a transitory, propagating signal.

Depiction of different features as modules is intended to highlight different functional aspects and does not necessarily imply that such modules must be realized by separate hardware or software components. Rather, functionality associated with one or more modules may be performed by separate hardware, firmware and/or software components, or integrated within common hardware, firmware and/or software components.

Figure 3:
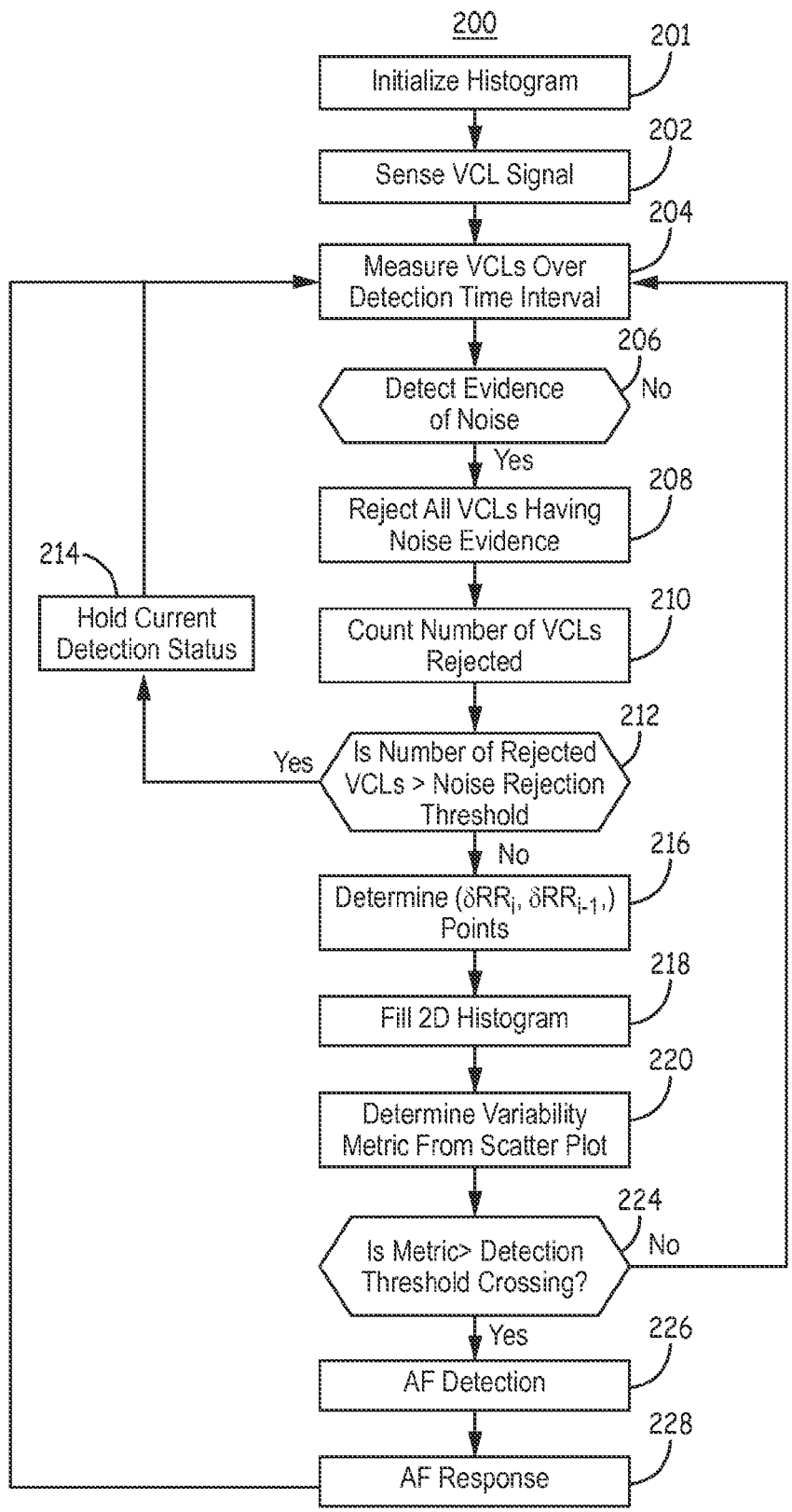
FIG. 3 is an exemplary flowchart of a method for detecting an atrial arrhythmia according to an embodiment of the disclosure.

FIG. 3 is an exemplary flowchart of a method for detecting an atrial arrhythmia according to an embodiment of the disclosure. Flow chart 200 illustrated in FIG. 3 and other flow charts presented herein are intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern implantable medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

Flow chart 200 is directed to atrial fibrillation (AF) detection, however it is recognized that aspects of the method may be applied to detection of other atrial arrhythmias, such as atrial flutter or other forms of atrial tachycardia. According to an embodiment of the present disclosure, the device includes a method and apparatus for detecting an atrial arrhythmia, such as atrial fibrillation or atrial flutter, for example. As illustrated in FIG. 3, according to one embodiment, the determination of an atrial arrhythmia may be based on the irregularity of ventricular cycles having RR intervals that exhibit discriminatory signatures when plotted in a Lorenz scatter plot, such as is generally disclosed by Ritscher et al. in U.S. Pat. No. 7,031,765, or in U.S. Pat. No. 8,639,316 to Sarkar, both incorporated herein by reference in their entireties. Other atrial arrhythmia determination methods are generally disclosed by Sarkar, et al. in U.S. Pat. No. 7,623,911 and in U.S. Pat. No. 7,537,569, and by Houben in U.S. Pat. No. 7,627,368, all of which patents are also incorporated herein by reference in their entireties.

In particular, at block 201, a histogram is initialized by defining the number of histogram bins for each coordinate axis and corresponding bin ranges. A counter for each histogram bin is set to zero. At block 202, a physiological signal containing VCL information is obtained. The signal may be an EGM or ECG signal but is not limited to being a cardiac electrical signal.

At block 204 the VCL intervals, e.g. RRIs, are collected over a predetermined rhythm detection time interval, for example for 2 minutes. Data collected over the established detection time interval is used to classify the rhythm at the end of the detection time interval. At block 206, a noise detection analysis is performed to detect evidence that a sensed R-wave signal or measured RRI contains noise artifact. Numerous noise detection methods may be used. Evidence of noise may detected based on frequency content, amplitude content, or VCL measurements themselves.

If no evidence of noise is detected in the predetermined time interval, the ($\delta RR_i$, $\delta RR_{i-1}$) data points are computed from the measured VCLs at block 216. If evidence of noise is detected, the VCLs that are associated with noise evidence are rejected at block 208. Any ($\delta RR_i$, $\delta RR_{i-1}$) data points that involve an RRI that is rejected will be skipped. Depending on the noise detection method being used, evidence of noise may be detected during the RRI between sensed R-waves or a sensed R-wave itself may be detected as noise. If a sensed R-wave is determined to be noise, both the preceding and subsequent RRIs defined by the sensed R-wave may be rejected as noise intervals.

The number of rejected VCLs is counted at block 210. The total number of VCLs (e.g. RRIs) rejected during the detection time interval due to noise is compared to a noise rejection threshold at block 212. If the noise rejection threshold is exceeded, the current rhythm detection status is held at block 214. The current time interval is considered to be too noisy for use in rhythm detection and no change in the status of the currently detected rhythm will be made based on the VCLs measured during the current time interval. For example, if the implantable medical device detected AF at the end of the last detection time interval based on the analysis of histogram counts, the AF detection will be maintained at the end of the current time interval. If the implantable medical device is not detecting AF at the end of the previous detection time interval, the implantable medical device remains in a state of no AF detection at the end of the current time interval. The current detection time interval is rejected as a whole for rhythm determination and classification. The process returns to block 204 to measure VCLs over the next detection time interval.

If the number of rejected cycle lengths has not reached a noise rejection threshold (block 212), the current detection time interval data is still used to populate a histogram defining a Lorenz plot area. At block 216, the ($\delta RR_i$, $\delta RR_{i-1}$) data points are determined using only RRIs that are not associated with noise evidence detection. Rejected RRIs are not used to compute RRI differences or ($\delta RR_i$, $\delta RR_{i-1}$) data points determined using rejected RRIs are skipped when populating the histogram. In this way, RRIs associated with noise aren't included in the analysis of VCLs in the Lorenz plot histogram. The remainder of the VCLs that are not rejected during the detection time interval are used for determining ($\delta RR_i$, $\delta RR_{i-1}$) data points. All ($\delta RR_i$, $\delta RR_{i-1}$) data points points not involving a rejected RRI may be used to populate the histogram. If a non-rejected VCL is sandwiched between two rejected VCLs, the VCL is not used because no adjacent non-rejected VCL is available for computing consecutive RRI differences for determining a valid ($\delta RR_i$, $\delta RR_{i-1}$) data point.

As described previously, a 2D scatter plot is generated wherein each point is defined by an x-coordinate corresponding to the difference between an RRI and the previous RRI and the y-coordinate corresponding to the difference between the previous RRI and the next previous RRI. The histogram is filled by incrementing a counter for the histogram bin which corresponds to the coordinate values of each ($\delta RR_i$, $\delta RR_{o-1}$) data point. The methods described herein are generally implemented using a 2D histogram, however aspects of the invention may alternatively be implemented in methods using 1D or higher dimensional scatter plots of VCL data.

At block 220 an RRI variability metric (or more generally a VCL variability metric) is determined from the scatter plot. Generally, the more histogram bins that are occupied, i.e. the more sparse the distribution of ($\delta RR_i$, $\delta RR_{i-1}$) points, the more irregular the VCL during the data acquisition time period. As such, a metric of the RRI variability can be used for detecting atrial fibrillation, which is associated with highly irregular VCL. In one embodiment, an RRI variability metric for detecting AF, referred to as an AF score is computed as generally described in the above-incorporated '911 patent. Briefly, the AF score may be defined by the equation:

AF Evidence=Irregularity Evidence−Origin Count−
PAC Evidence wherein Irregularity Evidence is the number of occupied histogram bins outside a Zero Segment defined around the origin of the Lorenz plot area. During normal sinus rhythm or highly organized atrial tachycardia, nearly all points will fall into the Zero Segment because of relatively small, consistent differences between consecutive RRIs. A high number of occupied histogram bins outside the Zero segment is therefore positive evidence for AF.

The Origin Count is the number of points in a "Zero Segment" defined around the Lorenz plot origin. A high Origin Count indicates regular RRIs, a negative indicator of AF, and is therefore subtracted from the Irregularity Evidence term. In addition, a regular PAC evidence score may be computed as generally described in the above-incorporated '911 patent. The regular PAC evidence score is computed based on a cluster signature pattern of data points that is particularly associated with PACs that occur at regular coupling intervals and present regular patterns of RRIs, e.g. associated with bigeminy (short-short-long RRIs) or trigeminy (short-short-short-long RRIs).

In other embodiments, an AF score or other RRI variability score for classifying an atrial rhythm may be computed as described in any of the above-incorporated '765, '911, '569 and '368 patents.

The AF score will be compared to an interval variation threshold for detecting AF, or AF detection threshold, at Block 224. If the metric crosses, i.e., the AF score is greater than the interval variation threshold, AF detection is made at block 226. A response to AF detection is made at block 228, which may include withholding a ventricular therapy, storing data, or triggering other signal acquisition or analysis, as described below. The AF response may be to generate a patient alarm or deliver or adjust a therapy. The RRI measurements continue to be performed after an AF detection to fill the histogram during the next detection time interval by returning to block 204.

After each detection time interval, the RRI variability metric is determined and the histogram bins are re-initialized to zero for the next detection time interval. The new RRI variability metric determined at the end of each data acquisition interval may be used to determine if the AF episode is sustained or terminated.

Figure 4:
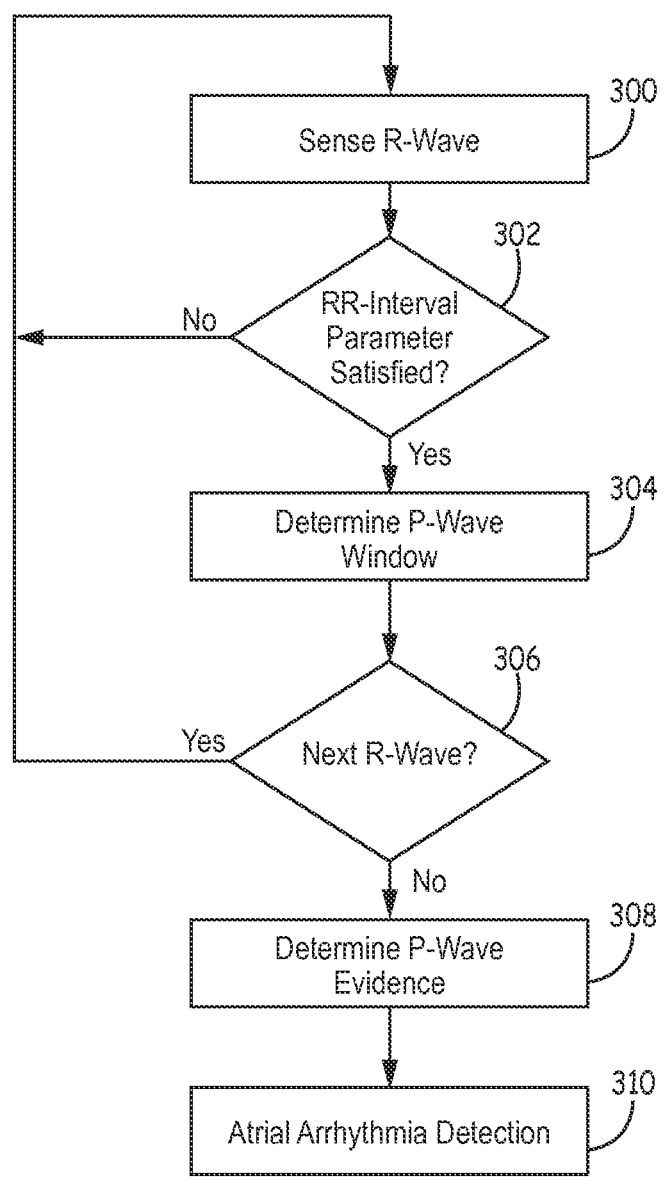
FIG. 4 is a flowchart of a method of augmenting detection of an atrial arrhythmia according to an embodiment of the present invention.

FIG. 4 is a flowchart of a method of augmenting detection of an atrial arrhythmia according to an embodiment of the present invention. As illustrated in FIG. 4, according to an embodiment of the present application, in order to determine whether a sensed cardiac signal is an atrial tachycardia event, once an AF event is determined to occur, the device determines whether the cardiac signal contains a P-wave portion, the results of which are utilized to augment the atrial tachycardia determination process described above. As illustrated in FIG. 4, according to one embodiment, during determination of signal characteristics for augmenting atrial tachycardia detection, the device senses the cardiac signal and identifies R-waves in response to the sensed cardiac signal using any known cardiac signal sensing and detection scheme, such as that disclosed in U.S. Pat. No. 5,117,824, by Keimel, et al., for example, described above and incorporated herein by reference in its entirety. Upon detection of an R-wave associated with the sensed cardiac signal, Block 300, the device determines whether the R-wave satisfies one or more RR-interval parameters, Block 302, described below. If the RR-interval parameter or parameters are not satisfied, No in Block 302, the device waits for the next sensed R-wave, Block 300 and the process Block 300-302 is repeated using the next R-wave. If the RR-interval parameter or parameters are satisfied, Yes in Block 302, the device determines a P-wave window associated with the R-wave, Block 304, as described below.

Upon determination of the P-wave window, the device determines whether a predetermined number of R-waves have been identified, Block 306. The predetermined number of R-waves required to satisfy the determination in Block 306 may be set as one or more R-waves, and according to one embodiment is set as four R-waves for example. If the predetermined number of R-waves have not been identified and therefore a next R-wave is needed, Yes in Block 306, the device waits for the next sensed R-wave, Block 300 and the process Block 300-306 is repeated using the next R-wave. If the predetermined number of R-waves have been identified and therefore a next R-wave is not needed, No in Block 306, the device determines P-wave evidence, Block 308, described below, and utilizes the determined P-wave evidence to augment atrial arrhythmia detection, Block 310, as described, for example, in commonly assigned U.S. patent application Ser. No. 14/695,111 to Sarkar et al., incorporated herein by reference in it's entirety.

Figure 5:
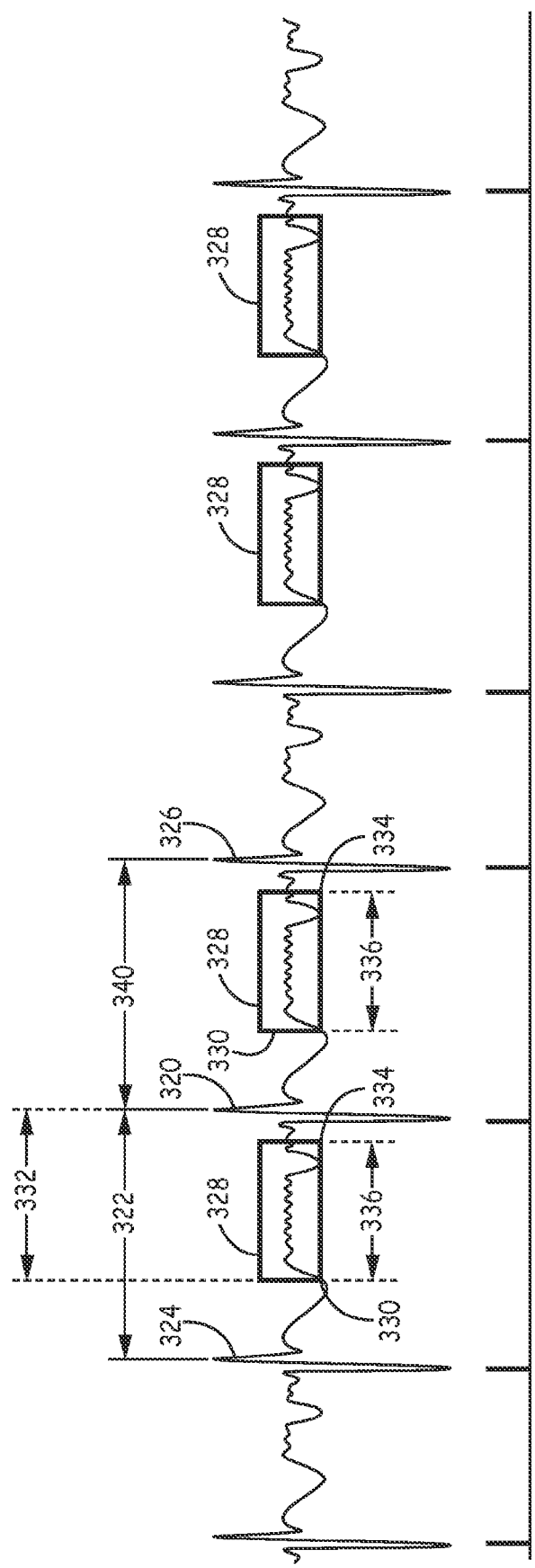
FIG. 5 is a schematic diagram of detecting an atrial arrhythmia according to an embodiment of the disclosure.

FIG. 5 is a schematic diagram of detecting an atrial arrhythmia according to an embodiment of the disclosure. As illustrated in FIGS. 4 and 5, in order to determine whether a sensed R-wave 320 satisfies the RR-interval parameters in Block 302, the device determines whether an RR interval 322 extending between the current R-wave 320 and a previous sensed R-wave 324 is greater than an interval threshold, such as 780 ms for example. If the RR interval 322 is not greater than the interval threshold, the RR-interval parameter is not satisfied, No in Block 302, and the process is repeated with the next RR interval 326. If the RR interval 322 is greater than the interval threshold, the RR interval parameter is satisfied, Yes in Block 302.

According to another embodiment, additional RR interval parameters may also be included in the determination as to whether the RR interval parameters have been satisfied in Block 302. For example, using R wave 326 as an example, in addition to the determination of whether the associated RR interval 340 satisfies the RR interval threshold, the device may also compare the RR interval 340 associated with the current R wave 326 with one or more previously determined RR intervals, such as interval 322 for example, and determine whether a relative change associated with the current RR-interval 340 is greater than a change threshold, such as 100 ms, for example. If the relative change associated with the current RR-interval is not greater than the change threshold, the RR interval parameter is not satisfied in Block 302. If the relative change associated with the current RR interval is greater than the change threshold, the RR-interval parameter is satisfied in Block 302.

In this way, if one of the RR intervals parameters are not satisfied, no P-wave window determination is made, and the process is repeated with the next R wave. If the RR interval parameter or one of the RR interval parameters are satisfied, the RR interval parameter is satisfied in Block 302, and the device determines a P wave window 328 associated with the R-wave 320 for determining whether the R wave 320 includes an associated P-wave. For example, in order to determine the P wave window 328, the device determines a P-wave window start point 330 located a predetermined distance 332 prior to the R-wave, such as 620 ms for example, and a P wave window endpoint 334 is located at a predetermined distance 336 subsequent to the P wave start point 330, such as 600 ms, for example, so that the P wave window 328 extends 600 ms between the P wave start point 330 and the P wave endpoint 334. Each time a P wave window 328 is determined, a P wave counter is updated by one, until the predetermined number of P wave windows are identified, such as four P wave windows, for example.

Figure 6:
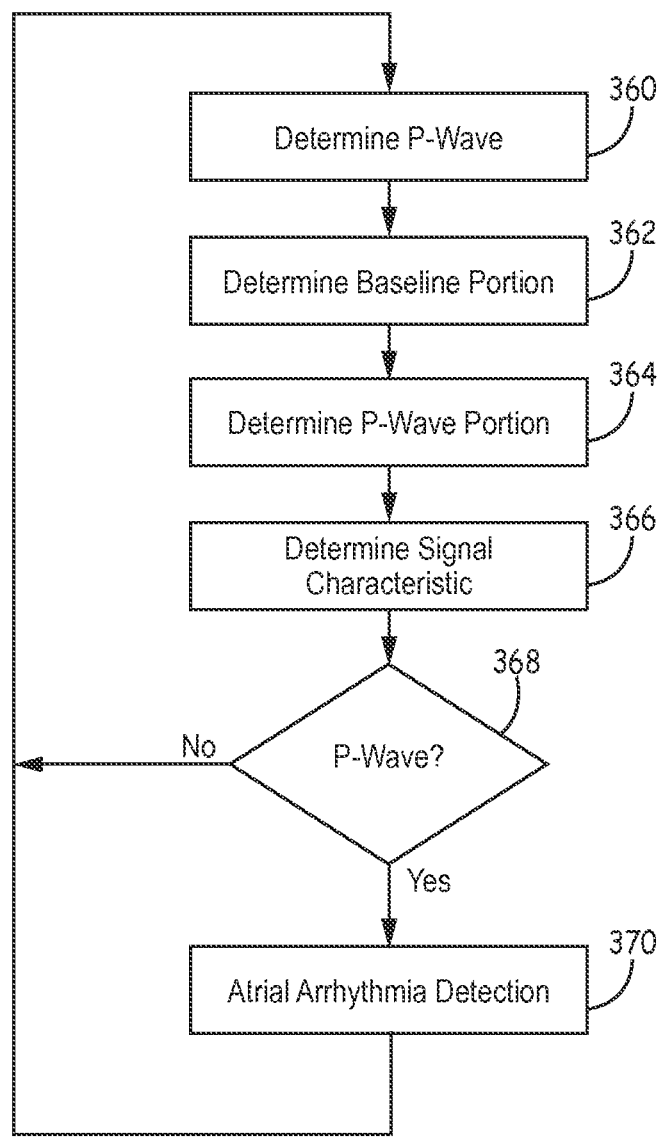
FIG. 6 is a flowchart of a method of detecting an atrial arrhythmia in a medical device according to an embodiment of the disclosure.

FIG. 6 is a flowchart of a method of detecting an atrial arrhythmia in a medical device according to an embodiment of the disclosure. In response to the predetermined number of P-waves being identified, No in Block 306 of FIG. 4, the device determines P-wave evidence for determining whether a P-wave is likely detected, Block 308, and utilizes the determined P-wave evidence to augment atrial arrhythmia detection, Block 310, described, for example, in commonly assigned U.S. patent application Ser. No. 14/695,111 to Sarkar et al., incorporated herein by reference in it's entirety. As illustrated in FIG. 6, during the determination of P-wave evidence, the device determines a characteristic P-wave in response to the current determined P-waves, Block 360. For example, according to one embodiment, the device determines an average P-wave from the four determined P-waves that is identified as the characteristic P-wave. The associated P-wave window is then divided into a baseline potion, Block 362, and a P-wave portion, Block 364, and determines signal characteristics, Block 366, for one or both of the baseline window and the P-wave window. A determination is then made, based on the determined signal characteristics, whether the characteristic P-wave is confirmed as being a P-wave, Block 368.

If the characteristic P-wave is not confirmed as being a P-wave, No in Block 368, the device waits for the next predetermined number of P-waves to be identified, Yes in Block 306 of FIG. 6, and the process, Blocks 360-368, is repeated using the next identified P-waves. If the characteristic P-wave is confirmed as being a P-wave, Yes in Block 368, the device utilizes the determination of a P-wave being present to augment atrial arrhythmia detection, Block 370, as described for example, in commonly assigned U.S. patent application Ser. No. 14/695,111 to Sarkar et al., incorporated herein by reference in it's entirety.

Figure 7:
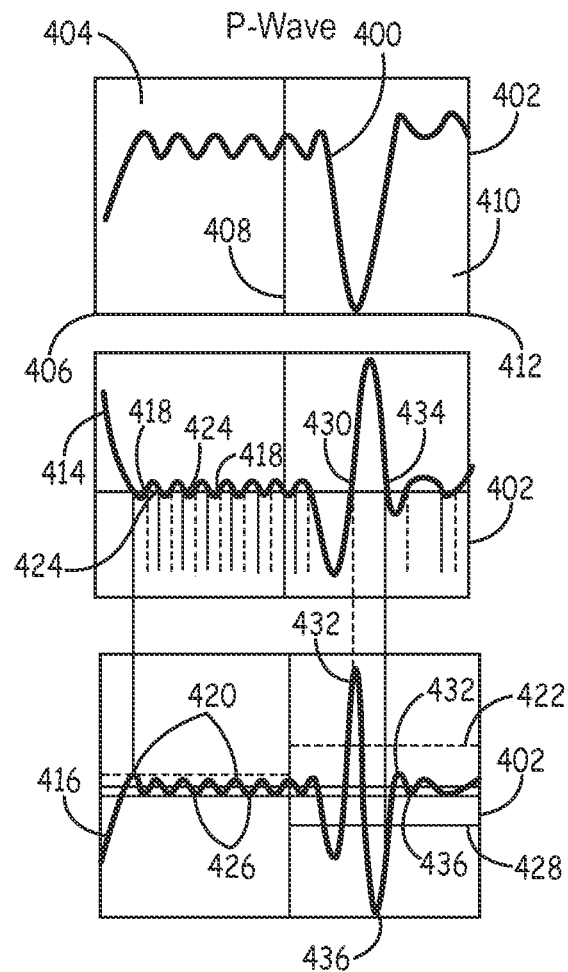
FIG. 7 is a schematic diagram of detecting an atrial arrhythmia in a medical device, according to an embodiment of the disclosure.

FIG. 7 is a schematic diagram of detecting an atrial arrhythmia in a medical device, according to an embodiment of the disclosure. As illustrated in FIGS. 6 and 7, in order to determine P-wave evidence (Block 308 of FIG. 4), the device determines a characteristic P-wave 400 having a characteristic P wave window 402 determined by averaging the determined four P-wave windows, as described above. The device divides the P-wave window 402 into a baseline portion 404, extending from the P-wave window start point 406 to a midpoint of the window 408, and a P-wave portion 410, extending from the midpoint of the window 408 to a P-wave window endpoint 412. The device determines a first derivative of the P-wave signal 414 and a second derivative of the p-wave signal 416, and determines corresponding second derivative values 420 associated with positive going zero crossings 418 of the first derivative signal 414 within the baseline portion 404 of the first derivative signal window 402. In one embodiment, the first derivative of the P wave signal can be computed as the difference between points separated by eight samples, and the second derivative can be computed as the difference between points separated by four sample in the first derivative.

The device determines the maximum amplitude of the second derivative values 420 associated with the positive going zero crossings 418, and the determined maximum amplitude value is then used to generate a first threshold 422 for evaluating the second derivative P-wave signal 416 within the P-wave portion 410 of the second derivative window 402. According to one embodiment, the threshold 422 is set as a multiple of the maximum of the second derivative values 420, such as twice the maximum of the second derivative values 420, for example.

In the same way, the device determines a corresponding second derivative value 426 for each negative going zero crossing 424 of the derivative signal 414 within the baseline portion 404 of the window 402. A minimum amplitude of the second derivative values 426 associated with the negative going first derivative zero crossings 424 is determined, and the determined minimum amplitude value is used to generate a second threshold 428 for evaluating the second derivative P-wave signal 416 within the P-wave portion 410 of the window 402. According to one embodiment, the threshold 428 is set as a multiple of the minimum of the second derivative values 426, such as twice the minimum of the second derivative values 426, for example.

Using the first threshold 422 determined in response to the determined maximum of the second derivative values 420, the device determines, for each positive going zero crossing 430 of the first derivative signal within the P-wave portion 410 of the first derivative window, a corresponding amplitude 432 of the second derivative signal within the P-wave portion 410 of the corresponding second derivative signal 416. The device compares the resulting maximum amplitudes 432 of the second derivative signal 416 signal within the P-wave portion 410 of the window 402 to the first threshold 422. Similarly, using the second threshold 422 determined in response to the determined minimum of the second derivative values 420, the device compares, for one or more negative going zero crossing 434 of the first derivative signal 414, the corresponding minimum amplitude 436 of the second derivative signal 416 signal within the P-wave portion 410 of the window 402 to the second threshold 428.

A P-wave is determined to have occurred, Yes in Block 368 of FIG. 6, if either the number of maximum amplitudes 432 determined to be greater than or equal to the first threshold 422 is equal to one, or the number of minimum amplitudes 432 determined to be less than or equal to the second threshold 428 is equal to one. If both the number of maximum amplitudes 432 determined to be greater than or equal to the first threshold 422 and the number of minimum amplitudes 432 determined to be less than or equal to the second threshold 428 is not equal to one, a P-wave is not determined to have occurred, No in Block 368 of FIG. 6. The result of the determination of whether a P-wave is identified is then used during the determination of an atrial arrhythmia event, as described for example, in commonly assigned U.S. patent application Ser. No. 14/695,111 to Sarkar et al., incorporated herein by reference in it's entirety.

As described above, during the arrhythmia detection scheme, the device initially determines whether to classify a rhythm as being either an atrial fibrillation event or as not being an atrial fibrillation event by determining the dispersion, or differences in patterns of RR intervals collected over a rhythm detection time interval, using a Lorentz scatter plot, for example. In order to reduce the number of false positives that occur during this initial determination of an atrial fibrillation event, the device augments the initial determination of atrial fibrillation by determining whether a P-wave occurs during the rhythm detection time intervals, as described above. If a P-wave is determined to occur, the initial determination that the cardiac signal sensed during the rhythm detection time interval was associated with an atrial fibrillation event for that rhythm detection time interval is identified as likely being a false determination of an atrial fibrillation episode, and therefore the device identifies the rhythm detection time interval as not being an atrial fibrillation event, as described above. On the other hand, if a P-wave is not determined to occur, the initial determination that the cardiac signal sensed during the rhythm detection time interval was associated with an atrial fibrillation event for that rhythm detection time interval is confirmed.

Figure 8:
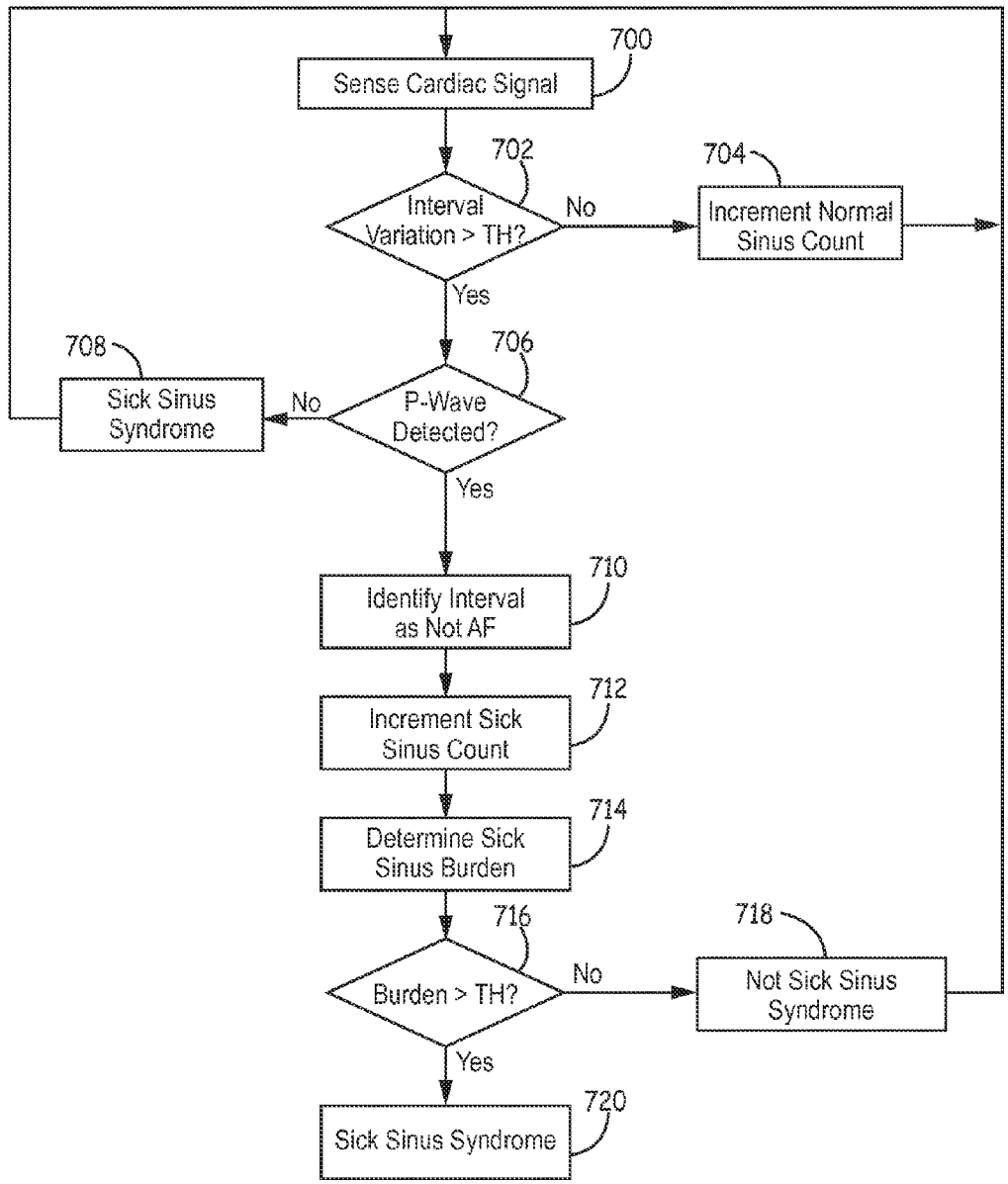
FIG. 8 is a flowchart of a method for determining a sick sinus burden in an implantable medical device, according to an embodiment of the present disclosure.

FIG. 8 is a flowchart of a method for identifying a sick sinus syndrome in an implantable medical device, according to an embodiment of the present disclosure. As illustrated in FIG. 8, in order to identify a patient as having sick sinus syndrome, the monitoring device 10 senses a cardiac signal, Block 700, and performs an initial atrial arrhythmia detection by determining the dispersion of RR intervals, or differences in patterns of RR intervals, for example, as described above.

In particular, the monitoring device 10 determines, as described above, whether the RR interval variation as defined by the AF evidence score determined for the two minute interval is greater than the AF detection threshold, Block 702. If it is determined that the RR interval variation is not greater than the AF detection threshold, No in Block 702, the device increments a normal sinus count, Block 704, and the process is repeated for the next two minute interval session, Blocks 700 and 702. If the interval variation is greater than the AF detection threshold, Yes in Block 702, the device determines whether evidence of the occurrence of a P-wave was determined during the two-minute interval, Block 706, as described above, for example. If evidence of the occurrence of a P-wave is not identified, No in Block 706, the two minute interval session is identified as being an atrial fibrillation event, Block 708, and the process is repeated for the next two minute interval session, Blocks 700 and 702.

If evidence of the occurrence of a P-wave is identified, Yes in Block 706, indicating both a high variability of RR intervals and a P-wave being sensed for the interval session, the two minute interval session is identified as not being an atrial fibrillation event, Block 710, and a sick sinus count is incremented, Block 712. For each instance in which the two minute interval session is identified as not being an atrial fibrillation event, Block 710, and the sick sinus count is incremented, Block 712, the monitoring device 10 determines a sick sinus burden, Block 714. For example, in order to determine the sick sinus burden in Block 714, the monitoring device 10 determines the number of two minute intervals determined to be associated with sick sinus syndrome. For example, according to one embodiment, the monitoring device 10 determines the sick sinus burden as being the percentage of two minute intervals during a predetermined time period, such as per day, or per hour, for example, that were identified as being sick sinus, i.e., the percentage of two minute intervals determined as including both high RR interval variability and a sensed P-wave.

The monitoring device 10 compares the sick sinus burden to a sick sinus burden threshold, Block 716, and determines whether the sick sinus burden is greater than the sick sinus burden threshold. For example, according to one embodiment, the sick sinus burden is set as a predetermined percentage during a given time period, such as 50 percent of the day, so that if the percentage of two minute intervals identified as being associated with sick sinus per day is not greater than 50 percent, No in Block 716, sick sinus syndrome is determined not to be occurring, Block 718, and the process is repeated for the next two minute interval session, Blocks 700 and 702. If the percentage of two minute intervals identified as being associated with sick sinus per day is greater than 50 percent, Yes in Block 716, sick sinus syndrome is determined to be occurring, Block 720. In other words, the patient is determined to be experiencing sick sinus syndrome, Block 720, if a ratio of sick sinus rhythm and normal sinus rhythm over a predetermined period of time, such as a day or an hour, for example, is greater than a predetermined threshold, i.e., 50 percent.

The monitoring device 10 stores the determination of whether or not the patient is experiencing sick sinus syndrome, which then may be used to determine whether the patient is a candidate for having a pacing device implanted, or whether the addition of a patient medication, or changes in a patient medication or medication dosage is indicated, and so forth. According to another embodiment, for example, the stored sick sinus information may be later accessed from the monitoring device 10 via a programmer or, according to yet another embodiment, the monitoring device 10 may transmit an alert signal indicating the presence of sick sinus syndrome, which would prompt the patient to seek a physician, who would then interrogate the monitoring device 10 and determine whether the patient is indicated for being implanted with a cardiac pacing device based on the stored sick sinus burden and/or the indication of interval sessions that are identified as being atrial fibrillation, normal sinus rhythm, sick sinus rhythm, or if the patient is identified as experiencing sick sinus syndrome.

Figure 9:
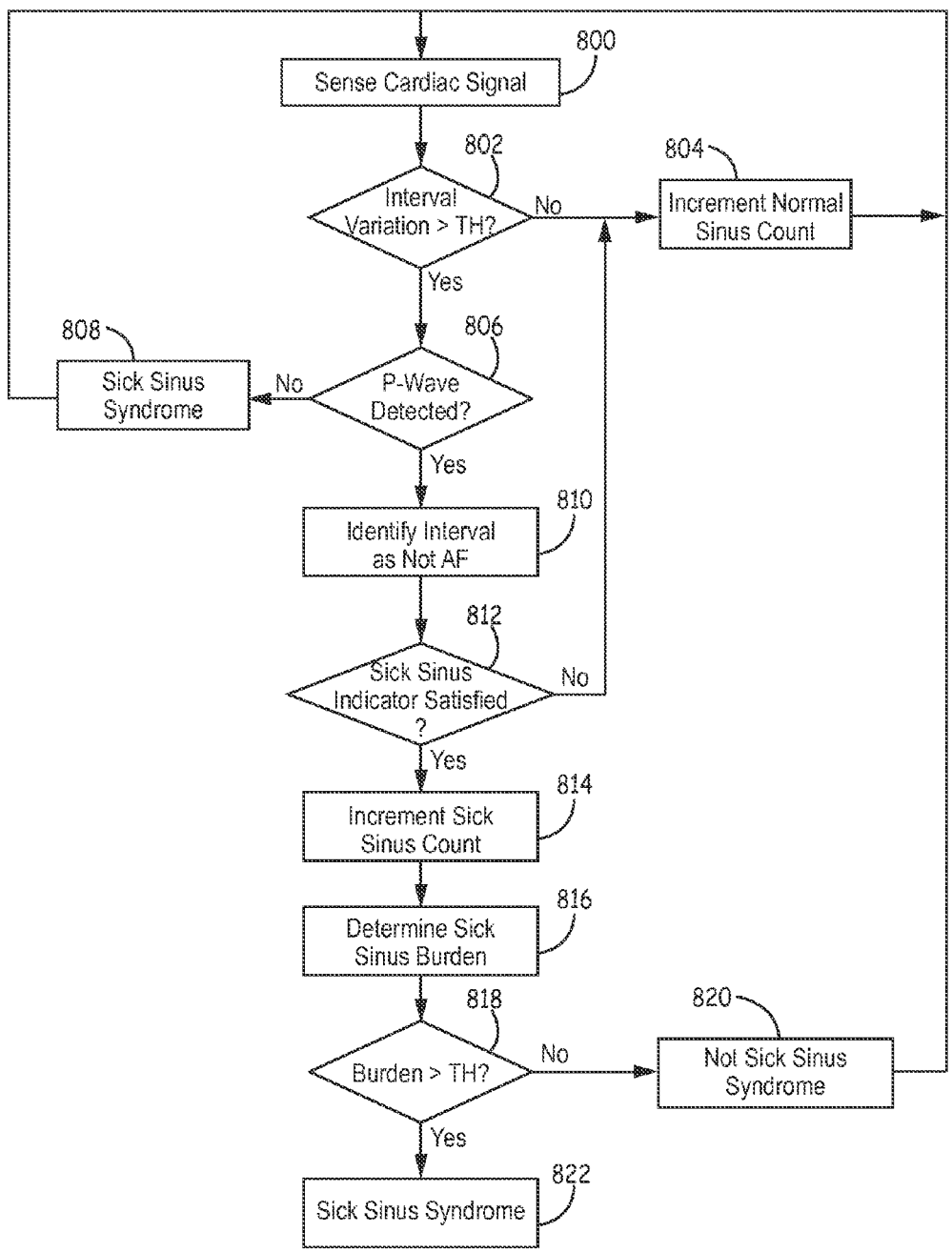
FIG. 9 is a flowchart of a method for determining a sick sinus burden in an implantable medical device, according to another embodiment of the present disclosure.

FIG. 9 is a flowchart of a method for identifying sick sinus syndrome in an implantable medical device, according to another embodiment of the present disclosure. As illustrated in FIG. 9, according to another embodiment, in order to identify a patient as having sick sinus syndrome, the monitoring device 10 senses a cardiac signal, Block 800, and performs an initial atrial arrhythmia detection by determining the dispersion of RR intervals, or differences in patterns of RR intervals, for example, as described above.

In particular, the monitoring device 10 determines, as described above, whether the interval variation as defined by the AF evidence score determined for the two minute interval is greater than the AF detection threshold, Block 802. If it is determined that the RR interval variation is not greater than the AF detection threshold, No in Block 802, the device increments a normal sinus count, Block 804, and the process is repeated for the next two minute interval session, Blocks 800 and 802. If the interval variation is greater than the AF detection threshold, Yes in Block 802, the device determines whether evidence of the occurrence of a P-wave was determined during the two-minute interval, Block 806, as described above, for example. If evidence of the occurrence of a P-wave is not identified, No in Block 806, the two minute interval session is identified as being an atrial fibrillation event, Block 808, and the process is repeated for the next two minute interval session, Blocks 800 and 802.

If evidence of the occurrence of a P-wave is identified, Yes in Block 806, the two minute interval session is identified as not being an atrial fibrillation event, Block 810, and the monitoring device 10 determines whether a sick sinus indicator is satisfied, Block 812. For example, according to one embodiment, the monitoring device may determine whether an interval rate associated with an RR interval of the RR intervals sensed during the two minute interval session is less than a predetermined interval threshold, such as 40 beats per minute, for example. According to another embodiment, the monitoring device 10 determines whether a predetermined number of RR intervals sensed during the two minute interval session having an interval rate less than a predetermined interval rate, such as five RR intervals or beats being less than 40 beats per minute. According to another embodiment, the monitoring device 10 determines whether a patient indicator was activated by the patient as a result of the patient experiencing symptoms such as fainting, dizziness, palpitations, shortness of breath, tiredness, or restlessness over a recent period of time, such as three days for example. According to yet another embodiment, the monitoring device 10 determines whether a combination of the patient indicator being activated and one or both the interval rate associated with an RR interval of the RR intervals sensed during the two minute interval session being less than a predetermined interval threshold and the predetermined number of RR intervals sensed during the two minute interval session having an interval rate less than a predetermined interval rate.

If the sick sinus indicator is not satisfied, No in Block 812, the normal sinus count is incremented, Block 804, and the process is repeated for the next two minute interval session, Blocks 800 and 802. If the sick sinus indicator is satisfied, Yes in Block 812, the sick sinus count is incremented, Block 814. For each instance in which the two minute interval session is identified as not being an atrial fibrillation event, Block 810, the sick sinus indicator is satisfied, Yes in Block 812, and the sick sinus count is incremented, Block 812, the monitoring device 10 determines a sick sinus burden, Block 816. For example, in order to determine the sick sinus burden in Block 816, the monitoring device 10 determines the number of two minute intervals determined to be associated with sick sinus syndrome. For example, according to one embodiment, the monitoring device 10 determines the sick sinus burden as being the percentage of two minute intervals during a predetermined time period, such as per day, or per hour, for example, that were identified as being sick sinus, i.e., the percentage of two minute intervals determined as having high RR interval variability and a sensed P-wave and additional sick sinus indicators such as symptoms and/or very slow RR intervals.

The monitoring device 10 compares the sick sinus burden to a sick sinus burden threshold, Block 818, and determines whether the sick sinus burden is greater than the sick sinus burden. For example, according to one embodiment, the sick sinus burden is set as 30 percent of the day so that if the percentage of two minute intervals identified as being associated with sick sinus is not greater than 30 percent, No in Block 818, sick sinus syndrome is determined not to be occurring, Block 820, the normal sinus count is incremented, Block 804, and the process is repeated for the next two minute interval session, Blocks 800 and 802. If the percentage of two minute intervals identified as being associated with sick sinus is greater than 30 percent, Yes in Block 818, sick sinus syndrome is determined to be occurring, Block 822. In other words, the patient is determined to be experiencing sick sinus syndrome, Block 822, if a ratio of sick sinus rhythm and normal sinus rhythm over a predetermined period of time, such as a day or an hour, for example, is greater than a predetermined threshold, i.e., 80 percent.

The monitoring device 10 stores the determination of whether or not the patient is experiencing sick sinus syndrome, which then may be used to determine whether the patient is a candidate for having a pacing device implanted, or whether the addition of a patient medication, or changes in a patient medication or medication dosage is indicated, and so forth. According to another embodiment, for example, the stored sick sinus information may be later accessed from the monitoring device 10 via a programmer. According to yet another embodiment, the monitoring device 10 may transmit an alert signal indicating the presence of sick sinus syndrome, which would prompt the patient to seek a physician, who would then interrogate the monitoring device 10 and determine the patient is indicated for being implanted with a cardiac pacing device if sick sinus syndrome is determined to be occurring.

According to another embodiment, during the determination as to whether the sick sinus burden is greater than the sick sinus burden threshold, Block 818, the monitoring device 10 may utilize various sick sinus burden thresholds during the determination of whether the sick sinus is identified, Block 882, depending upon the indicators that are used. For example, if a patient indicator is utilized, the threshold may be that the sick sinus burden threshold is set so that the number of two minute intervals that need to be identified as sick sinus is one of either 50 percent if the patient indicator is not activated, or 30 percent if the patient indicator is also activated during the two minute interval or over a predetermined time period, such as 3 day time period, for example.

Thus, an apparatus and method for determining a sick sinus burden have been presented in the foregoing description with reference to specific embodiments. It is appreciated that various modifications to the referenced embodiments may be made without departing from the scope of the invention as set forth in the following claims.

The invention claimed is:

1. A cardiac monitoring device for determining the occurrence of a sick sinus syndrome condition of a patient, comprising:
   a plurality of electrodes to sense a cardiac signal;
   a sensing module electrically coupled to the plurality of electrodes having circuitry positioned therein to receive the sensed cardiac signal; and
   a processor coupled to the sensing module and configured to determine an RR interval variability during an RR interval variability session in response to the sensed cardiac signal, determine whether a P-wave occurs during the RR interval variability session, determine whether a sick sinus indicator is satisfied in response to a P-wave occurring, increment a sick sinus count in response to the sick sinus indicator being satisfied, determine whether a sick sinus burden is satisfied in response to the sick sinus count being incremented, and determine the occurrence of sick sinus syndrome in response to the sick sinus burden being satisfied.

2. The cardiac monitoring device of claim 1, wherein the processor is configured to determine a percentage of a predetermined time period that is associated with the sick sinus count, compare the percentage of the predetermined time period to a sick sinus burden threshold, and determine whether the sick sinus threshold is satisfied in response to the comparing.

3. The cardiac monitoring device of claim 2, wherein the predetermined time period comprises one day and the sick sinus burden threshold comprises the sick sinus count being 50 percent per day.

4. The cardiac monitoring device of claim 1, wherein the processor determines whether the RR interval variability is greater than an RR variability threshold, increments a normal sinus count in response to the RR interval variability not being greater than the RR variability threshold, and determines whether the sick sinus burden is satisfied in response to a ratio of the sick sinus count and the normal sinus count.

5. The cardiac monitoring device of claim 1, wherein the processor is configured to determine a percentage of a predetermined time period that is associated with the sick sinus count, compare the percentage of the predetermined time period to a sick sinus burden threshold, and determine whether the sick sinus threshold is satisfied in response to the comparing and the sick sinus indicator being satisfied.

6. The cardiac monitoring device of claim 5, wherein the predetermined time period comprises one day and the sick sinus burden threshold comprises a first percentage value per day if the patient sick sinus indicator is not satisfied, and wherein the sick sinus burden threshold comprises a second percentage value per day if the patient sick sinus indicator is satisfied, wherein the second percentage value is less than the first percentage value.

7. The cardiac monitoring device of claim 1, wherein the processor is configured to determine whether an interval rate associated with an RR interval of the RR interval variability session is less than an interval rate threshold, and determine the sick sinus indicator is satisfied in response to an interval rate associated with an RR interval of the RR interval variability session being less than the interval rate threshold.

8. The cardiac monitoring device of claim 1, wherein the processor is configured to determine whether interval rates associated with a predetermined number of RR intervals of the RR interval variability session is less than an interval threshold, and determine the sick sinus indicator is satisfied in response to the predetermined number of RR intervals of the RR interval variability session being less than the interval threshold.

9. The cardiac monitoring device of claim 1, wherein the processor is configured to determine whether a patient indicator has been activated, determine whether an interval rate associated with an RR interval of the RR interval variability session is less than an interval rate threshold, determine whether interval rates associated with a predetermined number of RR intervals of the RR interval variability session is less than the interval rate threshold, and determine the sick sinus indicator is satisfied in response to the patient indicator being activated and one or both of the interval rate associated with an RR interval of the RR interval variability session being less than the interval rate threshold and interval rates associated with a predetermined number of RR intervals of the RR interval variability session being less than the interval rate threshold.

10. The cardiac monitoring device of claim 9, wherein the processor determines whether the RR interval variability is greater than an RR variability threshold, increments a normal sinus count in response to the RR interval variability not being greater than the RR variability threshold, and determines whether the sick sinus burden is satisfied in response to a ratio of the sick sinus count and the normal sinus count.

11. A method of determining the occurrence of a sick sinus syndrome condition of a patient, comprising:
   sensing a cardiac signal;
   determining an RR interval variability during an RR interval variability session in response to the sensed cardiac signal;
   determining whether a P-wave occurs during the RR interval variability session;
   determining whether a sick sinus indicator is satisfied in response to a P-wave occurring;
   incrementing a sick sinus count in response to the sick sinus indicator being satisfied;
   determining whether a sick sinus burden is satisfied in response to the sick sinus count being incremented; and
   determining the occurrence of sick sinus syndrome in response to the sick sinus burden being satisfied.

12. The method of claim 11, further comprising:
   determining a percentage of a predetermined time period that is associated with the sick sinus count;
   comparing the percentage of the predetermined time period to a sick sinus burden threshold; and
   determining whether the sick sinus threshold is satisfied in response to the comparing.

13. The method of claim 12, wherein the predetermined time period comprises one day and the sick sinus burden threshold comprises the sick sinus count being 50 percent per day.

14. The method of claim 11, further comprising:
   determining whether the RR interval variability is greater than an RR variability threshold;
   incrementing a normal sinus count in response to the RR interval variability not being greater than the RR variability threshold; and
   determining whether the sick sinus burden is satisfied in response to a ratio of the sick sinus count and the normal sinus count.

15. The method of claim 11, further comprising:
   determining a percentage of a predetermined time period that is associated with the sick sinus count;

comparing the percentage of the predetermined time period to a sick sinus burden threshold; and determining whether the sick sinus threshold is satisfied in response to the comparing and the sick sinus indicator being satisfied.

16. The method of claim 15, wherein the predetermined time period comprises one day and the sick sinus burden threshold comprises a first percentage value per day if the patient sick sinus indicator is not satisfied, and wherein the sick sinus burden threshold comprises a second percentage value per day if the patient sick sinus indicator is satisfied, wherein the second percentage value is less than the first percentage value.

17. The method of claim 11, further comprising:

determining whether an interval rate associated with an RR interval of the RR interval variability session is less than an interval rate threshold; and determining the sick sinus indicator is satisfied in response to an interval rate associated with an RR interval of the RR interval variability session being less than the interval rate threshold.

18. The method of claim 11, further comprising:

determining whether interval rates associated with a predetermined number of RR intervals of the RR interval variability session is less than an interval threshold; and determining the sick sinus indicator is satisfied in response to the predetermined number of RR intervals of the RR interval variability session being less than the interval threshold.

19. The method of claim 11, further comprising:

determining whether a patient indicator has been activated;

determining whether an interval rate associated with an RR interval of the RR interval variability session is less than an interval rate threshold;

determining whether interval rates associated with a predetermined number of RR intervals of the RR interval variability session is less than the interval rate threshold; and determining the sick sinus indicator is satisfied in response to the patient indicator being activated and one or both of the interval rate associated with an RR interval of the RR interval variability session being less than the interval rate threshold and interval rates associated with a predetermined number of RR intervals of the RR interval variability session being less than the interval rate threshold.

20. The method of claim 19, further comprising:

determining whether the RR interval variability is greater than an RR variability threshold;

incrementing a normal sinus count in response to the RR interval variability not being greater than the RR variability threshold; and determining whether the sick sinus burden is satisfied in response to a ratio of the sick sinus count and the normal sinus count.

* * * * *